United States Patent
Caylor, III

(10) Patent No.: US 8,632,464 B2
(45) Date of Patent: Jan. 21, 2014

(54) SYSTEM AND METHOD FOR MONITORING ORTHOPAEDIC IMPLANT DATA

(75) Inventor: Edward J. Caylor, III, Fort Wayne, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1861 days.

(21) Appl. No.: 11/530,567

(22) Filed: Sep. 11, 2006

(65) Prior Publication Data

US 2008/0071146 A1 Mar. 20, 2008

(51) Int. Cl.
*A61B 5/00* (2006.01)

(52) U.S. Cl.
USPC .................................. 600/300; 607/2; 482/8

(58) Field of Classification Search
USPC ........ 607/3, 129, 2; 600/300, 302; 623/16.11; 482/8
See application file for complete search history.

(56) References Cited

U.S. PATENT DOCUMENTS

| | | | |
|---|---|---|---|
| 4,352,960 A | 10/1982 | Dormer | |
| 4,436,684 A | 3/1984 | White | |
| 4,467,809 A | 8/1984 | Brighton | |
| 4,549,547 A | 10/1985 | Brighton et al. | |
| 4,573,475 A | 3/1986 | Dukes | |
| 4,830,021 A * | 5/1989 | Thornton | 600/520 |
| 4,936,862 A | 6/1990 | Walker | |
| 5,211,165 A | 5/1993 | Dumoulin et al. | |
| 5,300,120 A | 4/1994 | Knapp et al. | |
| 5,350,379 A | 9/1994 | Spievack | |
| 5,356,411 A | 10/1994 | Spievack | |
| 5,362,996 A | 11/1994 | Yizraeli | |
| 5,383,915 A | 1/1995 | Adams | |
| 5,448,489 A | 9/1995 | Reuben | |
| 5,488,952 A | 2/1996 | Schoolman | |
| 5,522,402 A | 6/1996 | Cooley | |
| 5,536,269 A | 7/1996 | Spievack | |
| 5,542,106 A * | 7/1996 | Krenz et al. | 455/575.7 |
| 5,610,996 A | 3/1997 | Eller | |
| 5,626,579 A | 5/1997 | Muschler et al. | |
| 5,662,111 A | 9/1997 | Cosman | |

(Continued)

FOREIGN PATENT DOCUMENTS

| | | |
|---|---|---|
| EP | 1 570 782 A2 | 3/2005 |
| EP | 1 571 581 A1 | 3/2005 |

(Continued)

OTHER PUBLICATIONS

D'Lima et al., 2005, "An implantable telemetry device to measure intra-articulartibial forces", Journal of Biomechanics, 38 pp. 299-304 (6 pages).

(Continued)

*Primary Examiner* — Scott Getzow
*Assistant Examiner* — Alyssa M Alter
(74) *Attorney, Agent, or Firm* — Barnes & Thornburg LLP

(57) ABSTRACT

A system and method for monitoring implant sensor data includes an orthopaedic implant, a patient exercise machine, and an antenna coupled to the patient exercise machine. The orthopaedic implant includes a sensor and a transmitter configured to transmit implant sensor data. The antenna is selected from a group of antennas based on the data rate and/or carrier frequency used by the transmitter. A controller is coupled to the antenna and configured to display the implant data, or indicia thereof, on a display device such as a computer monitor.

17 Claims, 9 Drawing Sheets

(56) References Cited

U.S. PATENT DOCUMENTS

| | | | |
|---|---|---|---|
| 5,704,939 A | 1/1998 | Justin | |
| 5,715,837 A | 2/1998 | Chen | |
| 5,741,215 A | 4/1998 | D'Urso | |
| 5,741,316 A | 4/1998 | Chen et al. | |
| 5,798,924 A | 8/1998 | Eufinger et al. | |
| 5,807,258 A | 9/1998 | Cimochowski et al. | |
| 5,832,488 A | 11/1998 | Eberhardt | |
| 5,855,609 A | 1/1999 | Knapp | |
| 5,961,553 A | 10/1999 | Coty et al. | |
| 6,002,859 A | 12/1999 | DiGioia et al. | |
| 6,034,296 A * | 3/2000 | Elvin et al. | 623/16.11 |
| 6,083,174 A | 7/2000 | Brehmeier-Flick et al. | |
| 6,115,636 A | 9/2000 | Ryan | |
| 6,126,690 A | 10/2000 | Ateshian et al. | |
| 6,144,385 A | 11/2000 | Girard | |
| 6,151,581 A | 11/2000 | Kraftson et al. | |
| 6,161,080 A | 12/2000 | Aouni-Ateshian et al. | |
| 6,177,034 B1 | 1/2001 | Ferrone | |
| 6,239,705 B1 | 5/2001 | Glen | |
| 6,254,639 B1 | 7/2001 | Peckitt | |
| 6,336,929 B1 | 1/2002 | Justin | |
| 6,366,799 B1 | 4/2002 | Acker et al. | |
| 6,369,694 B1 | 4/2002 | Mejia | |
| 6,400,272 B1 | 6/2002 | Holtzman | |
| 6,442,432 B2 | 8/2002 | Lee | |
| 6,447,448 B1 | 9/2002 | Ishikawa et al. | |
| 6,458,161 B1 | 10/2002 | Gibbs et al. | |
| 6,459,943 B1 | 10/2002 | Suetani et al. | |
| 6,474,599 B1 | 11/2002 | Stomski | |
| 6,480,745 B2 | 11/2002 | Nelson et al. | |
| 6,529,127 B2 | 3/2003 | Townsend | |
| 6,559,620 B2 | 5/2003 | Zhou et al. | |
| 6,565,576 B1 | 5/2003 | Stauch | |
| 6,574,511 B2 | 6/2003 | Lee | |
| 6,656,135 B2 | 12/2003 | Zogbi et al. | |
| 6,674,883 B1 | 1/2004 | Wei et al. | |
| 6,687,131 B1 | 2/2004 | Miehling | |
| 6,700,547 B2 | 3/2004 | Mejia et al. | |
| 6,720,930 B2 | 4/2004 | Johnson et al. | |
| 6,750,866 B1 | 6/2004 | Anderson, III | |
| 6,772,002 B2 | 8/2004 | Schmidt et al. | |
| 6,793,496 B2 | 9/2004 | Edic et al. | |
| 6,799,066 B2 | 9/2004 | Steines et al. | |
| 6,804,558 B2 | 10/2004 | Haller et al. | |
| 6,833,790 B2 | 12/2004 | Mejia et al. | |
| 6,847,892 B2 | 1/2005 | Zhou et al. | |
| 6,947,004 B2 | 9/2005 | Mejia et al. | |
| 7,015,826 B1 | 3/2006 | Chan et al. | |
| 7,191,007 B2 | 3/2007 | Desai et al. | |
| 7,191,013 B1 | 3/2007 | Miranda et al. | |
| 7,218,232 B2 | 5/2007 | DiSilvestro et al. | |
| 7,599,743 B2 | 10/2009 | Hassler, Jr. et al. | |
| 7,599,744 B2 | 10/2009 | Giordano et al. | |
| 2001/0051787 A1 | 12/2001 | Haller et al. | |
| 2002/0024450 A1 | 2/2002 | Townsend | |
| 2002/0065539 A1 * | 5/2002 | Von Arx et al. | 607/60 |
| 2002/0077562 A1 | 6/2002 | Kalgren et al. | |
| 2002/0128872 A1 | 9/2002 | Giammattei | |
| 2002/0135336 A1 | 9/2002 | Zhou et al. | |
| 2002/0151770 A1 | 10/2002 | Noll et al. | |
| 2002/0198740 A1 | 12/2002 | Roman et al. | |
| 2003/0045787 A1 | 3/2003 | Schulze et al. | |
| 2003/0067736 A1 | 4/2003 | Vahamaki et al. | |
| 2003/0069644 A1 | 4/2003 | Kovacevic | |
| 2003/0154411 A1 | 8/2003 | Hovik | |
| 2004/0008123 A1 | 1/2004 | Carrender | |
| 2004/0011137 A1 | 1/2004 | Hnat et al. | |
| 2004/0019384 A1 | 1/2004 | Kirking et al. | |
| 2004/0030395 A1 | 2/2004 | Blunn et al. | |
| 2004/0078219 A1 | 4/2004 | Kaylor et al. | |
| 2004/0106967 A1 | 6/2004 | Von Arx | |
| 2004/0113790 A1 | 6/2004 | Hamel et al. | |
| 2004/0133081 A1 * | 7/2004 | Teller et al. | 600/300 |
| 2004/0138663 A1 | 7/2004 | Kosashvili | |
| 2004/0138925 A1 | 7/2004 | Zheng | |
| 2004/0152972 A1 | 8/2004 | Hunter | |
| 2004/0171924 A1 | 9/2004 | Mire et al. | |
| 2004/0178955 A1 | 9/2004 | Menache et al. | |
| 2004/0230226 A1 | 11/2004 | Bingham | |
| 2005/0010299 A1 * | 1/2005 | Disilvestro | 623/18.12 |
| 2005/0010300 A1 | 1/2005 | Disilvestro et al. | |
| 2005/0012610 A1 | 1/2005 | Liao | |
| 2005/0027330 A1 | 2/2005 | Govari | |
| 2005/0055316 A1 | 3/2005 | Williams | |
| 2005/0065815 A1 | 3/2005 | Mazar | |
| 2005/0075697 A1 | 4/2005 | Olson et al. | |
| 2005/0091338 A1 | 4/2005 | de la Huerga | |
| 2005/0099290 A1 | 5/2005 | Govari | |
| 2005/0101962 A1 | 5/2005 | Schwenke et al. | |
| 2005/0113887 A1 | 5/2005 | Bauhahn | |
| 2005/0119716 A1 | 6/2005 | McClure et al. | |
| 2005/0165317 A1 | 7/2005 | Turner et al. | |
| 2005/0288739 A1 | 12/2005 | Hassler | |
| 2005/0288740 A1 | 12/2005 | Hassler | |
| 2005/0288741 A1 | 12/2005 | Hassler | |
| 2006/0009856 A1 | 1/2006 | Sherman | |
| 2006/0030945 A1 | 2/2006 | Wright | |
| 2006/0074319 A1 | 4/2006 | Barnes et al. | |
| 2006/0136013 A1 | 6/2006 | Sherman | |
| 2006/0190080 A1 | 8/2006 | Danoff | |
| 2007/0005141 A1 | 1/2007 | Sherman | |
| 2007/0179627 A1 | 8/2007 | Gustilo et al. | |
| 2007/0239282 A1 | 10/2007 | Caylor et al. | |
| 2008/0065225 A1 | 3/2008 | Wasielewski et al. | |

FOREIGN PATENT DOCUMENTS

| | | | |
|---|---|---|---|
| EP | 1 611 835 | A2 | 6/2005 |
| EP | 1 671 577 | A1 | 12/2005 |
| GB | 2 239 802 | A | 7/1991 |
| GB | 2272575 | A | 5/1994 |
| GB | 2 382 777 | A | 6/2003 |
| WO | 99/56614 | A1 | 11/1999 |
| WO | 00/13585 | A1 | 3/2000 |
| WO | 01/37926 | A1 | 5/2001 |
| WO | 01/49173 | A1 | 7/2001 |
| WO | 02/080753 | A2 | 10/2002 |
| WO | 02/091399 | A1 | 11/2002 |
| WO | 02/094113 | A1 | 11/2002 |
| WO | 2004/026399 | A1 | 4/2004 |
| WO | 2005/084544 | A1 | 9/2005 |
| WO | 2005/120203 | A2 | 12/2005 |

OTHER PUBLICATIONS

Graichen et al., 1999, "Implantable Telemetry System for Measurement of Hip Joint Force and Temperature", 15th Int. Symposium of Biotelemetry, Juneau, Alaska, US (Abstract).

Want, Roy, "RFID a Key to Automating Everything", Scientific American, Jan. 2004, pp. 56-65 (13 pages).

Extended European Search Report, European Application No. 07253590.9-1526, Apr. 28, 2011, 12 pages.

* cited by examiner

SYSTEM AND METHOD FOR MONITORING ORTHOPAEDIC IMPLANT DATA

TECHNICAL FIELD

The present disclosure relates generally to systems and methods for transmitting, receiving, and/or monitoring orthopaedic implant sensor data.

BACKGROUND

Orthopaedic implants are implanted into patients by orthopaedic surgeons to, for example, correct or otherwise alleviate bone and/or soft tissue loss, trauma damage, and/or deformation of the bone(s) of the patients. Some orthopaedic implants include one or more sensors for detecting or measuring various effects or forces acting on the orthopaedic implants and/or the surrounding environment. After initial implantation, it is often desirable by orthopaedic healthcare providers to periodically monitor the implant data generated by the implant sensors. Such data may, for example, predict or indicate orthopaedic implant wear or malfunction. To do so, the patient is typically required to perform a physical exercise while data from the implant sensor(s) is monitored. To allow the monitoring of the implant data, the patient is required to wear cumbersome electrical equipment near the site of the orthopaedic implant to provide power to electronics housed in the orthopaedic implant (e.g., the implant sensors) and/or to receive the data from the implant sensors. However, such cumbersome electrical equipment may alter the natural gait of the patient and thereby adversely affect the data obtained from the implant sensors.

SUMMARY

According to one aspect, a system for monitoring implant sensor data may include an orthopaedic implant. A sensor and a transmitter may be coupled to the orthopaedic implant. The sensor may be any type of sensor coupleable to the orthopaedic implant and capable of generating implant sensor data. For example, the sensor may be a pressure sensor, a load sensor, a temperature sensor, or a hall-effect sensor. The transmitter may be electrically coupled to the sensor. Additionally, the transmitter may be configured to wirelessly transmit the implant sensor data at a data rate of less than 100 kilobytes per second. The transmitter may transmit the implant sensor data using a predetermined carrier frequency of lower than 30,000 hertz.

The system may also include a patient exercise machine such as, for example, a treadmill, a stairstepper machine, a stationary bicycle, an elliptical trainer, a rowing machine, and a ski machine. The system may additionally include a loop antenna. The loop antenna may be coupled to the patient exercise machine, to the floor of an examination room, or to a movable structure. The loop antenna may be configured to receive the implant sensor data.

Further, the system may include a controller electrically coupled to the loop antenna. The controller may be configured to display the implant sensor data, or indicia thereof, on a display device such as a display screen of a computer. The controller may also be configured to record the implant sensor data. In some embodiments, the controller may be configured to transmit the implant sensor data to a database over a network and store the implant sensor data in the database. The system may also include a secondary coil and a primary coil. The secondary coil may be coupled to the orthopaedic implant and the primary coil may be electrically coupled to the controller. In such embodiments, the transmitter of the orthopaedic implant may be electrically coupled to the secondary coil and configured to transmit the implant sensor data in response to a power signal received from the secondary coil when the secondary coil is inductively coupled with the primary coil. In some embodiments, the transmitter may form a portion of a transceiver configured to receive programming data from the controller and transmit implant sensor data from one of a number of implant sensors selected based on the programming data.

According to another aspect, a system for monitoring implant sensor data may include an orthopaedic implant. A sensor and a transmitter may be coupled to the orthopaedic implant. The sensor may be any type of sensor coupleable to the orthopaedic implant and capable of generating implant sensor data. For example, the sensor may be a pressure sensor, a load sensor, a temperature sensor, or a hall-effect sensor. The transmitter may be electrically coupled to the sensor. Additionally, the transmitter may be configured to wirelessly transmit the implant sensor data at a data rate in the range of 100 kilobytes per second to 1,000 kilobytes per second. The transmitter may transmit the implant sensor data using a predetermined carrier frequency in the range of 30 megahertz to 2,000 mega hertz.

The system may also include a patient exercise machine such as, for example, a treadmill, a stairstepper machine, a stationary bicycle, an elliptical trainer, a rowing machine, and a ski machine. The system may additionally include a monopole antenna such as, for example, a quarter-wave monopole antenna, a half-wave monopole antenna, a five-eighths-wave monopole antenna, or the like. The monopole antenna may be coupled to the patient exercise machine, to the floor of an examination room, or to a movable structure. The monopole antenna may be configured to receive the implant sensor data.

Further, the system may include a controller electrically coupled to the monopole antenna. The controller may be configured to display the implant sensor data, or indicia thereof, on a display device such as a display screen of a computer. The controller may also be configured to record the implant sensor data. In some embodiments, the controller may be configured to transmit the implant sensor data to a database over a network and store the implant sensor data in the database. The system may also include a secondary coil and a primary coil. The secondary coil may be coupled to the orthopaedic implant and the primary coil may be electrically coupled to the controller. In such embodiments, the transmitter of the orthopaedic implant may be electrically coupled to the secondary coil and configured to transmit the implant sensor data in response to a power signal received from the secondary coil when the secondary coil is inductively coupled with the primary coil. In some embodiments, the transmitter may form a portion of a transceiver configured to receive programming data from the controller and transmit implant sensor data from one of a number of implant sensors selected based on the programming data.

According to yet another aspect, a system for monitoring implant sensor data may include an orthopaedic implant. A sensor and a transmitter may be coupled to the orthopaedic implant. The sensor may be any type of sensor coupleable to the orthopaedic implant and capable of generating implant sensor data. For example, the sensor may be a pressure sensor, a load sensor, a temperature sensor, or a hall-effect sensor. The transmitter may be electrically coupled to the sensor. Additionally, the transmitter may be configured to wirelessly transmit the implant sensor data at a data rate greater than 1,000 kilobytes per second. The transmitter may transmit the implant sensor data using a predetermined carrier frequency greater than 2 giga-hertz. In some embodiments, the transmitter may form a portion of a transceiver configured to receive programming data from the controller and transmit implant sensor data from one of a number of implant sensors selected based on the programming data.

The system may also include a patient exercise machine such as, for example, a treadmill, a stairstepper machine, a stationary bicycle, an elliptical trainer, a rowing machine, and a ski machine. The system may additionally include a patch antenna. The patch antenna may be coupled to the patient exercise machine, to the floor of an examination room, or to a movable structure. The patch antenna may be configured to receive the implant sensor data.

Further, the system may include a controller electrically coupled to the patch antenna. The controller may be configured to display the implant sensor data, or indicia thereof, on a display device such as a display screen of a computer. The controller may also be configured to record the implant sensor data. In some embodiments, the controller may be configured to transmit the implant sensor data to a database over a network and store the implant sensor data in the database. The system may also include a secondary coil and a primary coil. The secondary coil may be coupled to the orthopaedic implant and the primary coil may be electrically coupled to the controller. In such embodiments, the transmitter of the orthopaedic implant may be electrically coupled to the secondary coil and configured to transmit the implant sensor data in response to a power signal received from the secondary coil when the secondary coil is inductively coupled with the primary coil. In some embodiments, the transmitter may form a portion of a transceiver configured to receive programming data from the controller and transmit implant sensor data from one of a number of implant sensors selected based on the programming data.

BRIEF DESCRIPTION OF THE DRAWINGS

The detailed description particularly refers to the following figures, in which.

DETAILED DESCRIPTION OF THE DRAWINGS

Figure 1:
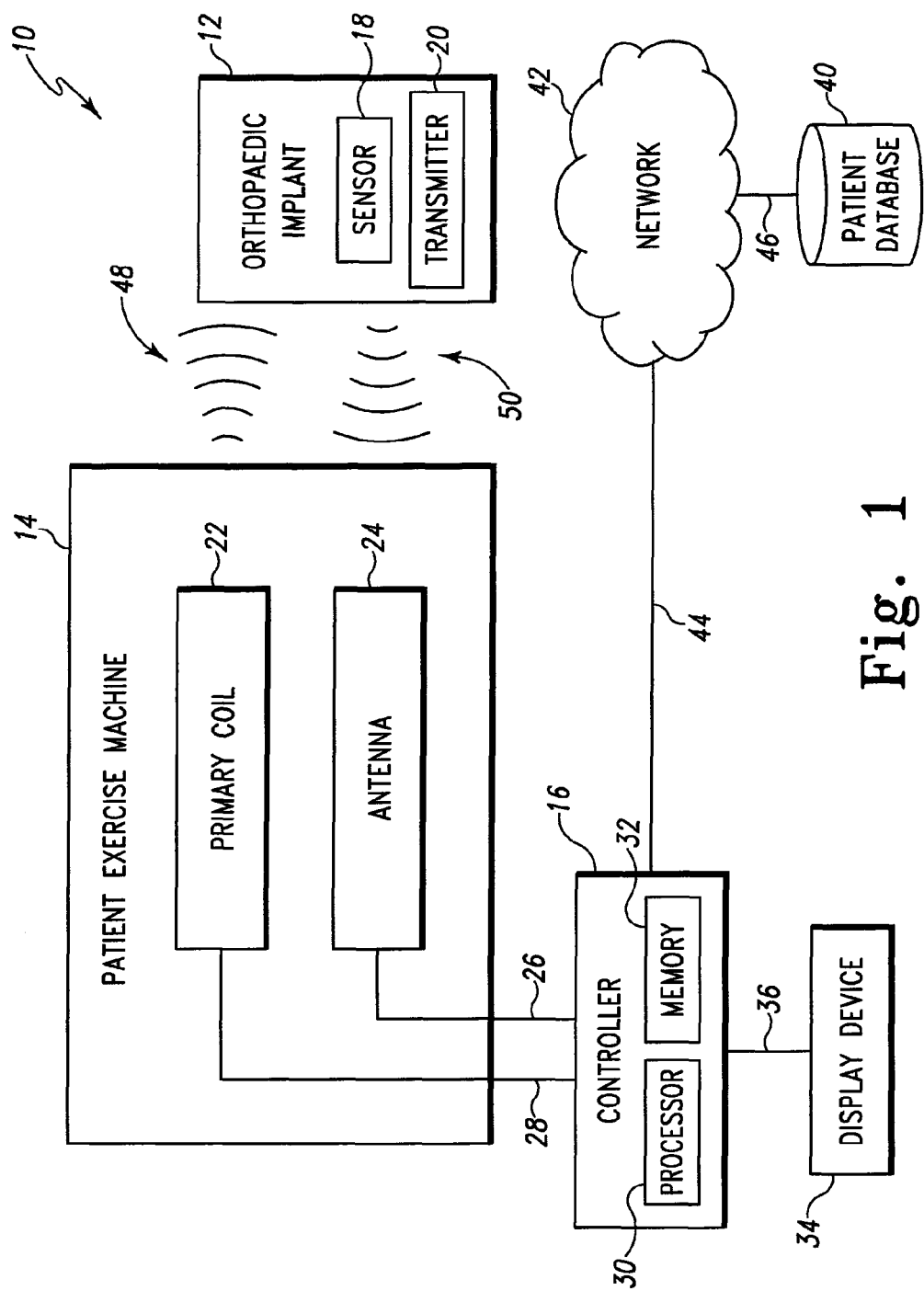
FIG. 1 is a simplified block diagram of a system for monitoring implant sensor data.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 2:
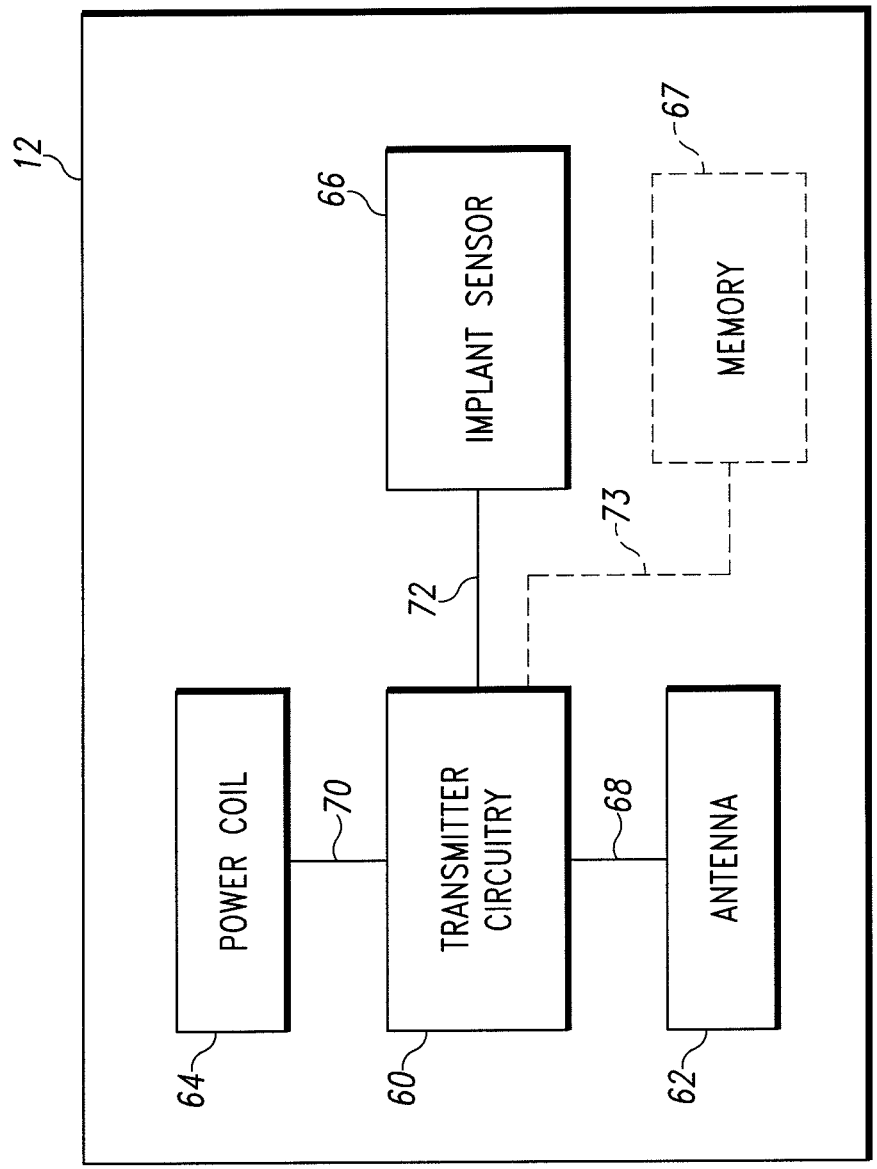
FIG. 2 is a simplified block diagram of one embodiment of an orthopaedic implant of the system of FIG. 1.
Figure 3:
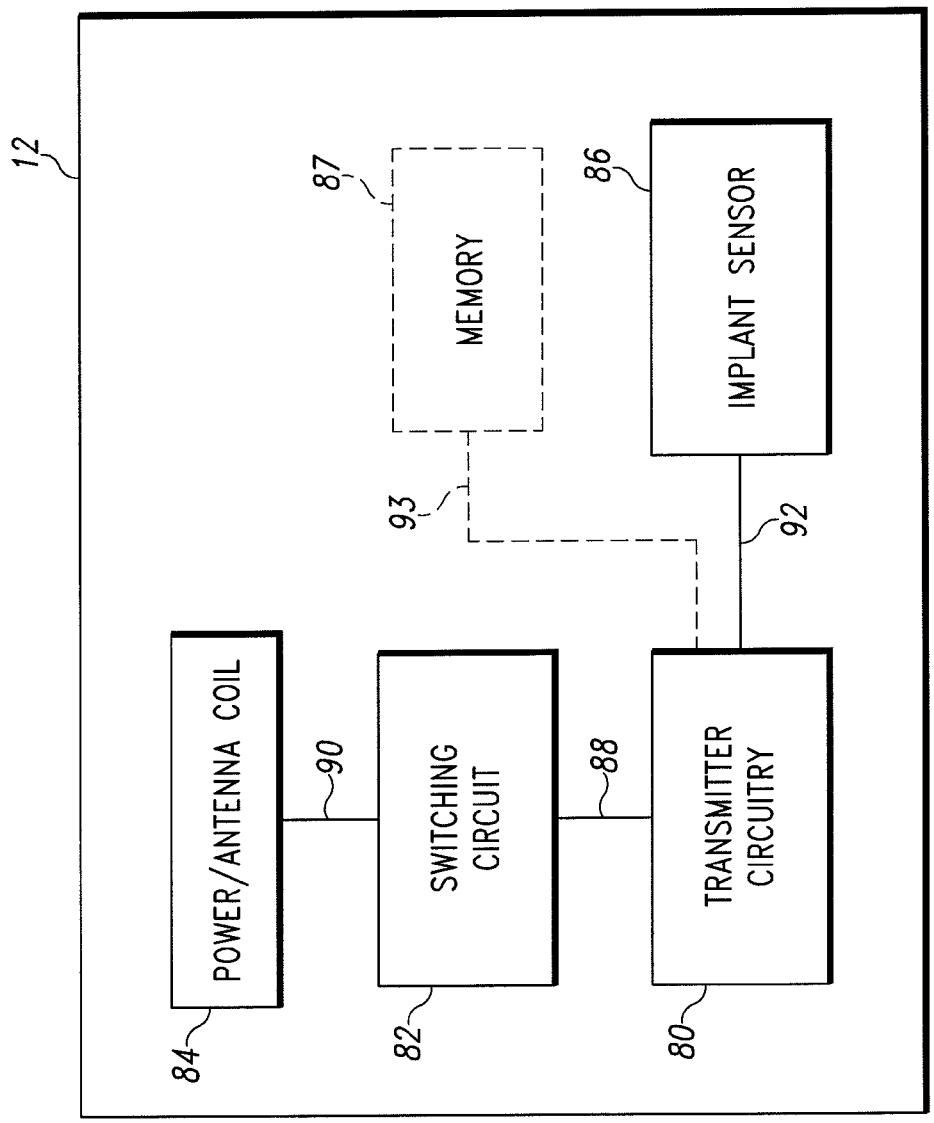
FIG. 3 is a simplified block diagram of another embodiment of an orthopaedic implant of the system of FIG. 1.

Referring to FIG. 1, a system 10 for monitoring implant sensor data includes an orthopaedic implant 12, a patient exercise machine 14, and a controller 16. The orthopaedic implant 12 may be embodied as any type of orthopaedic implant such as, for example, a knee implant, a hip implant, a shoulder implant, or the like. An implant sensor 18, a transmitter 20, and other circuitry, as discussed in more detail below in regard to FIGS. 2 and 3, are coupled to or otherwise housed in the orthopaedic implant 12. The implant sensor 18 may be embodied as any type of sensor capable of generating implant sensor data of a parameter of interest. For example, the implant sensor 18 may be embodied as a pressure sensor, a load sensor, a temperature sensor, a hall-effect sensor, or the like. It should be appreciated that although only a single sensor 18 is illustrated in FIG. 1, in other embodiments, the system 10 may include any number of similar and/or different implant sensors coupled to or housed in the orthopaedic implant 12.

The transmitter 20 may be embodied as or include any type of transmitter circuitry capable of transmitting the implant sensor data at a predetermined data rate or within a predetermined data rate range using a predetermined carrier frequency or range of frequencies. It should be appreciated that depending on the type and number of sensors used, the parameter of interest, the type and format of the implant sensor data, and the sampling rate employed, the transmitter 20 may be configured to transmit the implant data at any one or more of a number of different data rates and using any one or more of a number of different carrier frequencies.

The patient exercise machine 14 may be embodied as any type of exercise machine on which the patient may exercise. For example, the patient exercise machine 14 may be embodied as a treadmill, a stairstepper machine, a stationary bicycle, an elliptical trainer, a rowing machine, a ski machine, or the like. In the illustrative embodiment of FIG. 1, a primary coil 22 and an antenna 24 are coupled to the patient exercise machine 14. The primary coil 22 may be embodied as any type of primary coil capable of being inductively coupled to a secondary coil (not shown in FIG. 1) housed in or coupled to the orthopaedic implant 12 and generating a current therein.

Although described above as being coupled to the patient exercise machine, in other embodiments, the primary coil 22 may be portable rather than coupled to the patient exercise machine 14. For example, in some embodiments, the primary coil 22 is configured to be held by a healthcare provider and in the vicinity of the implant 12 while the patient is exercising on the patient exercise machine 14. In such embodiments, the primary coil 22 may embodied as, for example, a toroidal primary coil configured to receive a limb of the patient or a "c"-shaped primary coil configured to be held by a healthcare provider as described in detail in U.S. patent application Ser. No. 11/172,316 entitled "APPARATUS, SYSTEM, AND METHOD FOR TRANSCUTANEOUSLY TRANSFERRING ENERGY," which was filed on Jun. 30, 2005 by Jason T. Sherman, the entirety of which is expressly incorporated herein by reference. In another embodiment, the primary coil 22 includes two patches couplable to the skin of the patient in the vicinity of the orthopaedic implant 12. The patches each include a Helmholtz-like coil and are powered such that the Helmholtz coils produce an isotropic magnetic field, which is received by the secondary coil of the implant 12.

The antenna 24 may be embodied as a loop antenna, a monopole antenna, or a patch antenna depending upon the data rate and/or carrier frequency utilized by the transmitter 20 and/or sensor 18. That is, as described in more detail below in regard to FIGS. 4-6, the antenna 24 is selected based the predetermined data rate or range of data rates and/or carrier frequency or range of frequencies used by the orthopaedic implant 12. As such, the antenna 24 may have an increased sensitivity, a reduced size, or the like compared to other antennas used in a particular embodiment.

The antenna 24 is communicatively coupled to the controller 16 via communication links 26. Similarly, the primary coil 22 is communicatively coupled to the controller 16 via communication links 28. The communications links 24, 26 may be embodied as any type of communication links capable of facilitating electrical communication between the antenna 24 and the controller 16 and between the primary coil 22 and the controller 16, respectively. For example, the communication link 24, 26 may be embodied as or otherwise include any number of wires, cables, printed circuit board traces, vias, and/or the like.

The controller 16 includes a processor 30 and a memory device 32. The processor 30 may be embodied as any type of processor including, for example, discrete processing circuitry (e.g., a collection of logic devices), general purpose integrated circuit(s), and/or application specific integrated circuit(s) (i.e., ASICs). The memory device 32 may be embodied as any type of memory device and may include one or more memory types, such as, random access memory (i.e., RAM) and/or read-only memory (i.e., ROM). In addition, the controller 16 may include other devices and circuitry typically found in a computer for performing the functions described herein such as, for example, a hard drive, input/output circuitry, and the like.

The controller 16 is communicatively coupled with a display device 34 via a communication link 36. Although illustrated in FIG. 1 as separate from the controller 16, the display device 34 may form a portion of the controller 16 in some embodiments. Additionally or alternatively, the display device 34 or an additional display device may be positioned away from the controller 16. For example, the display device 34 may be coupled with the ceiling or wall of the examination room wherein the orthopaedic examination procedure is to be performed. Additionally or alternatively, the display device 34 may be embodied as a virtual display such as a holographic display, a body mounted display such as a heads-up display, or the like. The controller 16 may also be coupled with a number of input devices such as a keyboard and/or a mouse for providing data input to the controller 16.

The controller 16 is also communicatively coupled to a patient database 40 via a network 42. The patient database 40 may be embodied as any type of database capable of storing patient-related data. Although illustrated in FIG. 1 as a single database, it should be appreciated that the patient database 40 may be embodied as any number of separate databases, file folders, flat files, or other storage locations. Such patient-related data may include, for example, the implant sensor data received from the orthopaedic implant 12 and other data derived therefrom such as graphs, charts, and the like. The patient-related data may be stored in the database 40 in association with, indexed by, or otherwise retrievable based on patient identification data such as the patient's name, address, etc. The patient database 40 may be located in the doctor's office or hospital wherein the system 10 is incorporated or may be located remotely therefrom. In one particular embodiment, the patient database 40 forms a portion of a hospital network that is accessible by the controller 16 via the network 42.

The network 42 may be embodied as any type of network capable of facilitating communication between the controller 16 and the patient database 40. For example, the network 42 may be a local area network (LAN), a wide area network (WAN), or form a portion of a publicly-accessible, global network such as the Internet. In addition, the network 42 may be a wired network, a wireless network, or a combination thereof. In one particular embodiment, the network 42 is embodied as or forms a portion of a hospital network and, as such, may include additional computers, routers, communication links, and/or the like.

The controller 16 is communicatively coupled to the network 42 via a number of communication links 44. Similarly, the patient database 40 is communicatively coupled to the network 42 via any number of communication links 46. The communication links 44, 46 may be any type of communication links capable of facilitating communication between the controller 16 and the patient database 40. For example, the communication links 44, 46 may be embodied as any number of wires, cables such as fiber optic cables, or the like. Additionally, any one or more of the communication links 44, 46 may be embodied as wired or wireless communication links. In embodiments wherein the communication links 44, 46 are wireless communication links, the controller 16 and/or the patient database 40 may include a wireless transmitter and/or receiver to facilitate wireless communication with the network 42.

In operation, the system 10 is usable by a healthcare provider such as an orthopaedic surgeon, doctor, or nurse to monitor implant sensor data received from the orthopaedic implant 12. To do so, the controller 16 is configured to provide a power signal to the primary coil 22 via the communication link 28. The primary coil 22 is located in a position near the orthopaedic implant 12, which is implanted in the patient, while the patient is operating the patient exercise machine 14. The primary coil 22 may be so positioned by an orthopaedic healthcare provider or, in some embodiments, may be coupled to the patient exercise machine 14 in an appropriate location. Regardless, the primary coil 22 is positioned in such a location that an electromagnetic field 48 generated by the primary coil 22 is capable of inductively coupling the primary coil 22 and a secondary coil located in or coupled to the orthopaedic implant 12. Once so inductively coupled, the transmitter 20 is configured to transmit implant sensor data received from the sensor 18 to the antenna 24 via a wireless communication link 50. As discussed above, the transmitter 20 may be configured to transmit the implant sensor data at a data rate or range of data rates and/or at a carrier frequency or range of frequencies based on, for example, the type and number of implant sensors used, the parameter of interest, the type and format of the implant sensor data, and the sampling rate employed. The controller 16 receives the implant data via the antenna 24 and communication link 26. The controller 16 may be configured to display the implant sensor data, indicia thereof, or other data determined based on the implant sensor data on the display device 34. For example, the controller 16 may be configured to display a graph or chart determined based on the implant data on the display device 34. To do so, the controller 16 may be configured to store the implant data in the memory device 32. Alternatively or additionally, the controller 16 may be configured to transmit the implant data to the patient database via the network 42 for storage therein.

Referring now to FIG. 2, in one embodiment, the orthopaedic implant 12 includes a transmitter circuit 60, an antenna 62, a power coil 64, and one or more implant sensors 66. The transmitter circuit 60 is communicatively coupled to the antenna 62 via a number of communication links 68, to the power coil 64 via a number of communication links 70, and to the implant sensor(s) 66 via a number of communication links 72. The communication links 68, 70, 72 may be embodied as any type of communication links capable of facilitating communication between the transmitter circuit 60 and the antenna 62, power coil 64, and the implant sensor(s) 66, respectively. For example, the communication links 68, 70, 72 may be embodied as wires, cables, printed circuit board (PCB) traces, fiber optic cables, or the like.

Similar to the transmitter 20 discussed above in regard to FIG. 1, the transmitter circuit 60 may be embodied as or include any type of transmitter circuitry capable of transmitting the implant sensor data received from the implant sensor(s) 66 at a predetermined data rate or within a predetermined data rate range using a predetermined carrier frequency or range of frequencies. The particular data rate or range of data rate used may be determined based on, for example, the type and number of implant sensors 66 used, the parameter of interest, the type and format of the implant sensor data, and the sampling rate employed. For example, in one embodiment, the transmitter circuit 60 is configured to transmit the implant sensor data using a data rate less than 100 kilobytes per second. In another embodiment, the transmitter circuit 60 is configured to transmit the implant sensor data using a data rate in the range of 100 kilobytes per second to 1,000 kilobytes per second. In a further embodiment, the transmitter circuit 60 is configured to transmit the implant sensor data using a data rate greater than 1,000 kilobytes per second.

Additionally, the transmitter circuit 60 may be configured to transmit the implant sensor data using a predetermined carrier frequency or range of frequencies. For example, in one embodiment, the transmitter circuit 60 is configured to transmit the implant sensor data using a frequency or range of frequencies in or below the Very Low Frequency (VLF) band (e.g., using a frequency below 30,000 hertz). Alternatively, in another embodiment, the transmitter circuit 60 is configured to transmit the implant sensor data using a frequency or range of frequencies in the Very High Frequency (VHF) or the lower Ultra High Frequency (UHF) band (e.g., using a frequency in the range of 30 mega-hertz to 2,000 mega-hertz). Still further, in another embodiment, the transmitter circuit 60 is configured to transmit the implant sensor data using a frequency or range of frequencies in the higher Ultra High Frequency (UHF) band (e.g., using a frequency greater than 2 giga-hertz).

In some embodiments, the transmitter circuitry 60 may include additional circuitry such as processing circuitry or the like. However, in other embodiments, the transmitter circuit 60 may be embodied as a simple inductor-capacitor (LC) circuit or a crystal oscillator circuit and associated circuitry.

The transmitter circuit 60 receives power via the power coil 64. The power coil 64 is configured to be inductively coupled to the primary coil 22 when the primary coil 22 receives a power signal from the controller 16. The power coil 64 may include any number of individual coils. For example, the power coil 64 may include a single coil that is inductively coupled to the external primary coil 22 by positioning the primary coil 22 near the skin of the patient such that the power coil 64 lies within the alternating current (AC) electromagnetic field 48 generated by the primary coil 22. In other embodiments, the power coil 64 includes more than a single coil to thereby improve the inductive coupling of the power coil 64 and the primary coil 22. That is, because the amount of inductive coupling of the power coil 64 and the primary coil 22 is dependent upon the alignment of the power coil 64 and the electromagnetic field generated by the primary coil 22, a secondary coil having multiple coils at different orientations decreases the likelihood of poor inductive coupling with the external power source. For example, in one embodiment, the power coil 64 is embodied as three separate coils positioned orthogonally with respect to each other. As discussed above in regard to FIG. 1, the primary coil 22 may be embodied as any type of power source capable of inductively coupling with the power coil 64 and generating a current therein.

Similar to the implant sensor 18 described above in regard to FIG. 1, the implant sensor 66 may be embodied as any number and type of sensor(s) capable of generating implant sensor data of a parameter of interest. For example, the implant sensor 66 may be embodied as a pressure sensor, a load sensor, a temperature sensor, a hall-effect sensor, or the like. The implant sensor 66 may continually, periodically, or responsively generate the implant data. For example, in some embodiments, the implant sensor 66 is configured to generate the implant data only while the power coil 64 is inductively coupled to the primary coil 22.

In some embodiments, the orthopaedic implant 12 also includes a memory device 67. In such embodiments, the memory device 67 is communicatively coupled to the transmitter circuitry 60 via a number of communication links 73, which may be embodied as any type of communication links capable of facilitating communication between the transmitter circuitry 60 and the memory device 67 such as, for example, wires, cables, printed circuit board (PCB) traces, fiber optic cables, or the like. The memory device 67 may be embodied as any type of memory device and may include one or more memory types, such as, random access memory (i.e., RAM) and/or read-only memory (i.e., ROM). In such embodiments, the transmitter circuitry 60, or other processing circuit, may be configured to store implant sensor data received from the implant sensor(s) 66 in the memory device 67. The stored implant sensor data may be subsequently retrieved from the memory device 67 and transmitted via the transmitter circuitry 60 as discussed above.

Referring now to FIG. 3, in another embodiment, the orthopaedic implant 12 includes a transmitter circuit 80, a switching circuit 82, a power/antenna coil 84, and one or more implant sensors 86. The transmitter circuit 80 is communicatively coupled to the switching circuit 82 via a number of communication links 88 and to the implant sensor(s) 86 via a number of communication links 92. The switching circuit 82 is coupled to the power/antenna coil 84 via a number of communication links 90. Similar to the communication links 68, 70, 72 described above in regard to FIG. 2, the communication links 88, 90, 92 may be embodied as any type of communication links capable of facilitating communication between the transmitter circuit 80, the switching circuit 82, the power/antenna coil 84, and the implant sensor(s) 86. For example, the communication links 88, 90, 92 may be embodied as wires, cables, printed circuit board (PCB) traces, fiber optic cables, or the like.

The transmitter circuit 80 is substantially similar to the transmitter 60 described above in regard to FIG. 2 and, as such, may be embodied as or include any type of transmitter circuit capable of transmitting the implant sensor data received from the implant sensor(s) 86 at a predetermined data rate or within a predetermined data rate range using a predetermined carrier frequency or range of frequencies. The particular data rate or range of data rate used may be determined based on, for example, the type and number of implant sensors 86 used, the parameter of interest, the type and format of the implant sensor data, and the sampling rate employed.

For example, in one embodiment, the transmitter circuit 80 is configured to transmit the implant sensor data using a data rate less than 100 kilobytes per second. In another embodiment, the transmitter circuit 80 is configured to transmit the implant sensor data using a data rate in the range of 100 kilobytes per second to 1,000 kilobytes per second. In a further embodiment, the transmitter circuit 80 is configured to transmit the implant sensor data using a data rate greater than 1,000 kilobytes per second.

Additionally, the transmitter circuit 80 may be configured to transmit the implant sensor data using a predetermined carrier frequency or range of frequencies. For example, in one embodiment, the transmitter circuit 80 is configured to transmit the implant sensor data using a frequency or range of frequencies in or below the Very Low Frequency (VLF) band (e.g., using a frequency below 30,000 hertz). Alternatively, in another embodiment, the transmitter circuit 80 is configured to transmit the implant sensor data using a frequency or range of frequencies in the Very High Frequency (VHF) or the lower Ultra High Frequency (UHF) band (e.g., using a frequency in the range of 30 mega-hertz to 2,000 mega-hertz). Still further, in another embodiment, the transmitter circuit 80 is configured to transmit the implant sensor data using a frequency or range of frequencies in the higher Ultra High Frequency (UHF) band (e.g., using a frequency greater than 2 giga-hertz).

In some embodiments, the transmitter circuitry 80 may include additional circuitry such as processing circuitry or the like. However, in other embodiments, the transmitter circuit 80 may be embodied as a simple inductor-capacitor (LC) circuit or a crystal oscillator circuit and associated circuitry.

Similar to the implant sensor 66 described above in regard to FIG. 2, the implant sensor 86 may be embodied as any number and type of sensor capable of generating implant sensor data of a parameter of interest. For example, the implant sensor 86 may be embodied as a pressure sensor, a load sensor, a temperature sensor, a hall-effect sensor, or the like. The implant sensor 86 may be continually, periodically, or responsively generate the implant data. For example, in some embodiments, the implant sensor 86 is configured to generate the implant data only while the power/power coil 64 is inductively coupled to the primary coil 22.

In the embodiment illustrated in FIG. 3, the transmitter circuit 80 receives power and transmits the implant data the same coil, i.e., the power/antenna coil 84. To do so, the switching circuit 82 is operable to connect the power/antenna coil 84 to a power terminal(s) or port of the transmitter circuit 80 when power is to be provided thereto and to connect the power/antenna coil 84 to an output terminal(s) or port of the transmitter circuit 80 when power is not being provided and transmission of the wireless signal is desired. For example, the switching circuit 82 may include a coil or other device responsive to the magnetic field generated by the primary coil 22 to switch the connection of the power/antenna coil 84 from the output terminal of the transmitter circuit 80 to the power terminal. As such, when the primary coil 22 is positioned near the skin of the patient in the vicinity of the orthopaedic implant 12, the power/antenna coil 84 is inductively coupled with the primary coil 22 and connected to the power terminal of the transmitter circuit 80 via the switching circuit 82.

As discussed above in regard to FIG. 3, the orthopaedic implant 12 may also include a memory device 87 in some embodiments. The memory device 87 is communicatively coupled to the transmitter circuitry 80 via a number of communication links 93, which may be embodied as any type of communication links capable of facilitating communication between the transmitter circuitry 80 and the memory device 87 such as, for example, wires, cables, printed circuit board (PCB) traces, fiber optic cables, or the like. The memory device 87 may be embodied as any type of memory device and may include one or more memory types, such as, random access memory (i.e., RAM) and/or read-only memory (i.e., ROM). In such embodiments, the transmitter circuitry 80, or other processing circuit, may be configured to store implant sensor data received from the implant sensor(s) 86 in the memory device 87. The stored implant sensor data may be subsequently retrieved from the memory device 87 and transmitted via the transmitter circuitry 80 as discussed above.

Figure 4:
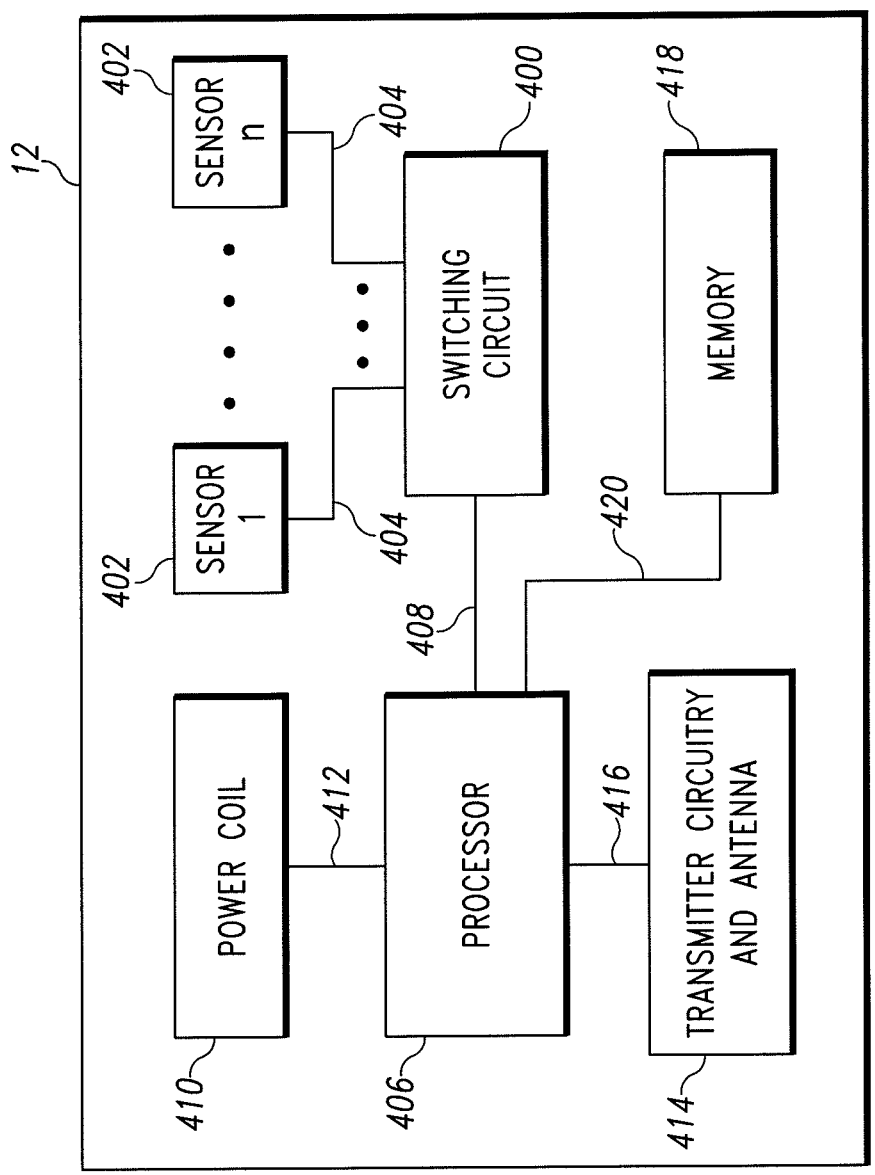
FIG. 4 is a simplified block diagram of another embodiment of an orthopaedic implant of the system of FIG. 1.

As discussed above in regard to FIGS. 2 and 3, the orthopaedic implant 12 may include more than one implant sensor 18, 66, 86 in some embodiments. In such embodiments as illustrated in FIG. 4, the orthopaedic implant 12 may include a switching circuit 400 communicatively coupled to each implant sensor 402 via a number of communication links 404. The switching circuit 400 is controlled by a processor 406 to selectively couple any one or more of the implant sensors 402 to the processor 406 via a number of communication links 408. The processor 406 is also communicatively coupled to a power coil 410, a transmitter circuitry and antenna 414, and a memory device 418 via a number of communication links 412, 416, 420, respectively. The communication links 404, 408, 412, 416, and 420 may be any type of communication capable of facilitating electrical communication between the devices of the orthopaedic implant 12. For example, the communication links 404, 408, 412, 416, 420 may be embodied as or otherwise include any number of wires, cables, printed circuit board traces, vias, and/or the like.

The processor may be embodied as any type of processor including, for example, discrete processing circuitry (e.g., a collection of logic devices), general purpose integrated circuit(s), and/or application specific integrated circuit(s) (i.e., ASICs). The memory device 418 is similar to the memory devices 67, 87 described above in regard to FIGS. 2 and 3 and may be embodied as any type of memory device and include one or more memory types, such as, random access memory (i.e., RAM) and/or read-only memory (i.e., ROM). Similarly, the power coil 410 is substantially similar to the power coil 64 described above in regard to FIG. 2 and is configured to be inductively coupled to the primary coil 22 when the primary coil 22 receives a power signal from the controller 16. The transmitter circuitry and antenna 414 is substantially similar to the transmitter circuitry 60 and antenna 62 described above in regard to FIG. 2 and, as such, may be embodied as or include any type of transmitter circuit capable of transmitting the implant sensor data received from the implant sensor(s) 402 at a predetermined data rate or within a predetermined data rate range using a predetermined carrier frequency or range of frequencies. It should be appreciated that although the orthopaedic implant 12 illustrated in FIG. 4 includes a separate power coil 410 and transmitter antenna, in other embodiments, a power/antenna coil similar to the power/antenna coil 84 illustrated in and described above in regard to FIG. 3 may be used instead.

In use, the processor 406 is configured to be responsive to a control signal received from the transmitter circuitry 414 to control the switching circuit 400. The processor 406 may control the switching circuit 400 to thereby couple any one or more of the sensors 402 to the processor 406 such that the processor 406 receives the implant sensor data from the coupled sensors 402. In this way, the orthopaedic implant 12 may be programmed to transmit data from all of the sensors 402 or from a selective number of the sensors 402. As such, an orthopaedic healthcare provider is able to monitor the implant sensor data from any one or more of the sensors 402 as described in more detail below in regard to FIGS. 8 and 9.

Although the embodiments of the orthopaedic implant 12 described above in regard to FIGS. 2, 3, and 4 each receive power via the primary coil 22, in some embodiments, the orthopaedic implant 12 includes an internal power source (not shown). The internal power source may be embodied as, for example, a battery or the like and electrically coupled to the transmitter circuit 60, 80 or processor 406 to provide power thereto.

Figure 5:
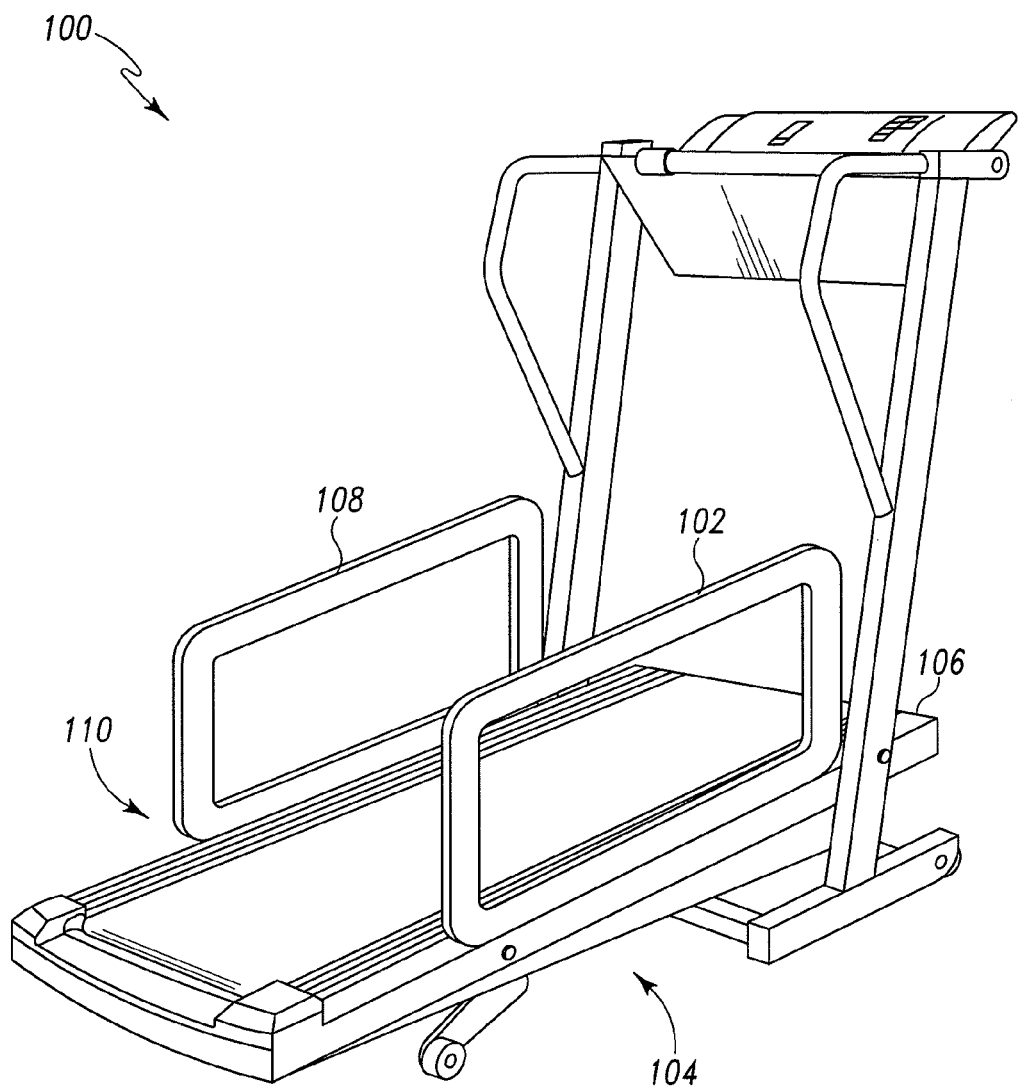
FIG. 5 is a perspective view of one embodiment of a patient exercise machine of the system of FIG. 1.
Figure 6:
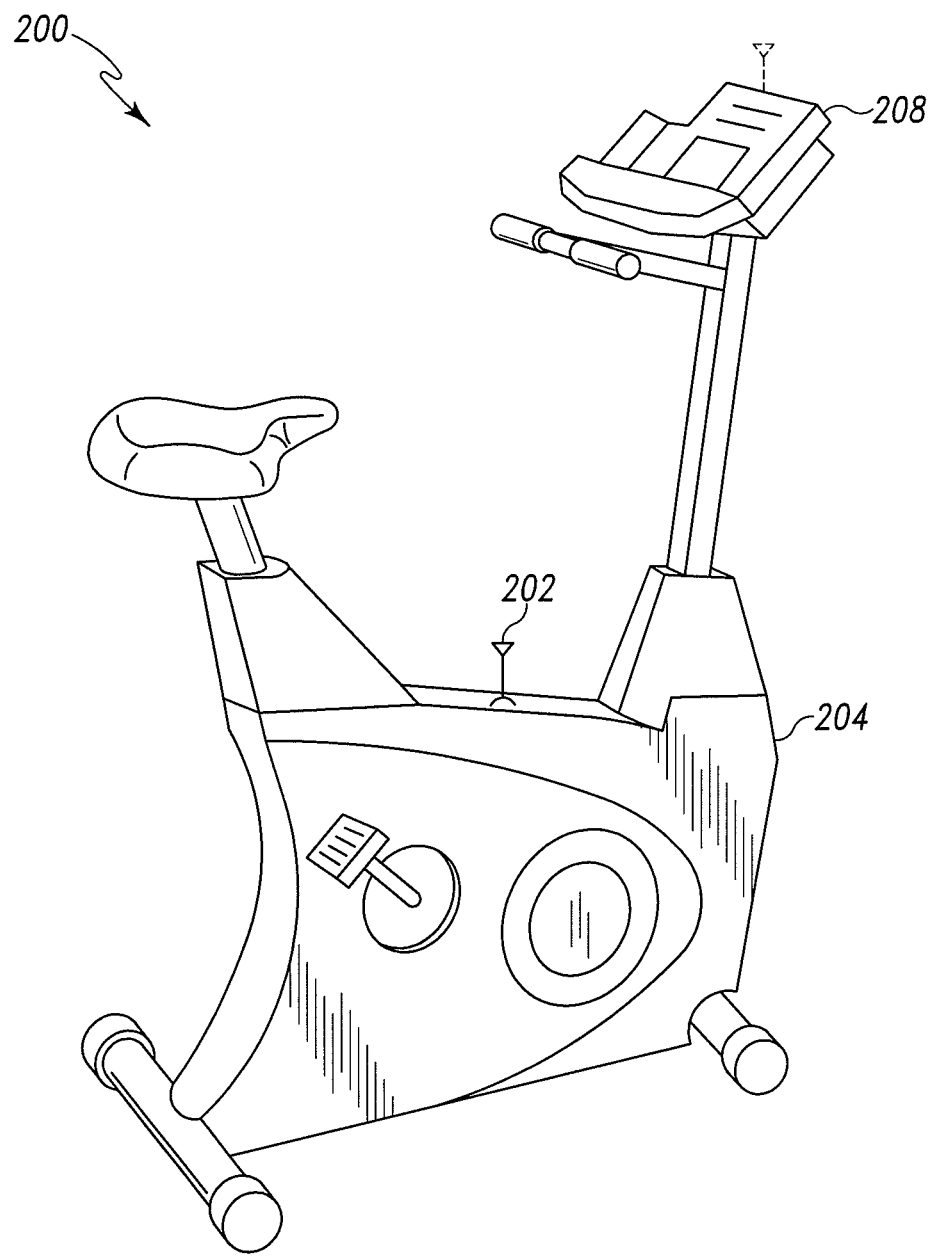
FIG. 6 is a perspective view of another embodiment of a patient exercise machine of the system of FIG. 1.
Figure 7:
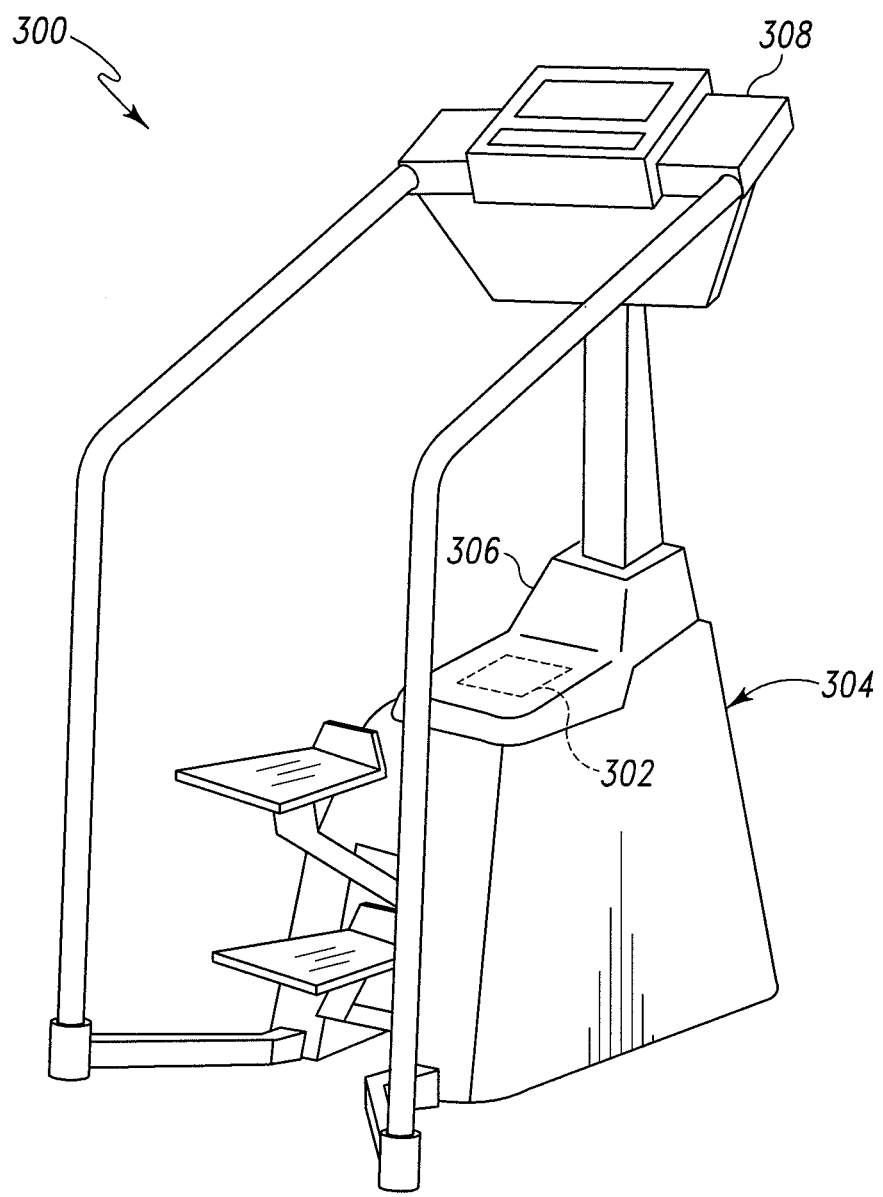
FIG. 7 is a perspective view of another embodiment of a patient exercise machine of the system of FIG. 1.

Referring now to FIGS. 5-7, several embodiments of particular patient exercise machines will be described. It should be appreciated, however, that the type of patient exercise machines so described are only exemplary and that, in other embodiments, other types of patient exercise machines may be used with any of the combination of antennas, transmitters, implant sensors, data rates, and/or carrier frequencies described below.

As illustrated in FIG. 5, in one embodiment, the patient exercise machine 14 is embodied as a treadmill 100. The treadmill 100 includes a loop antenna 102 coupled to a first longitudinal side 104 of a frame 106 of the treadmill 100. The loop antenna 102 is coupled to the frame 106 in a location such that the loop antenna 102 is in the vicinity of the orthopaedic implant 12 when the patient is operating the treadmill 100. For example, in the illustrative embodiment of FIG. 5, the loop antenna 102 is positioned for communication with orthopaedic implants 12 located in the lower portion of the body of the patient (e.g., a knee implant). However, in other embodiments, the loop antenna 102 may be positioned for communication with orthopaedic implants 12 located in other portions of the patient's body. For example, in embodiments wherein the implant 12 is an orthopaedic shoulder implant, the loop antenna 102 may be coupled to the frame 106 in a more upwardly location. Additionally, in some embodiments, the loop antenna 102 may be movably coupled to the frame 106 such that the location of the loop antenna 102 relative to the patient may be altered. To improve reception from the orthopaedic implant 12, in some embodiments, the treadmill 100 may include a second loop antenna 108 coupled to a second longitudinal side 110 of the frame 106.

It should be appreciated that the treadmill 100 is configured for communication with an orthopaedic implant 12 using a relatively low data rate and carrier frequency. That is, in embodiments of the system 10 wherein the sensor 18, 66, 86 is configured to generate the implant sensor data at a data rate of less than 100 kilobytes per second and/or the transmitter 20, 60, 80, 414 is configured to transmit the implant sensor data using a carrier frequency lower than 30,000 hertz, the antenna 24 of the patient exercise machine 14 is embodied as a loop antenna (e.g., loop antenna 102). Because a relatively lower carrier frequency (e.g., below 30,000 hertz) is used, the implant data signal transmitted by the transmitter 20, 60, 80, 414 may be less attenuated due to passage of the signal through skin of the patient. The use of a lower carrier frequency may also reduce the amount of heat generated. In addition, because a relatively lower data rate (e.g., less than 100 kilobytes per second) is used in the illustrative embodiment, a relatively lower carrier frequency (e.g., less than 30,000 hertz) may be used because of the small bandwidth required to transmit the lower amount of data. As such, it should be appreciated that the reception of the system 10 may be improved by use of a loop antenna when a relatively low data rate (e.g., less than 100 kilobytes per second) and/or a relatively low carrier frequency (e.g., less than 30,000 hertz) are used due to the improved sensitivity of a loop antenna to low frequency and low power signals.

Again, it should be appreciated that although the embodiment of FIG. 5 has been illustrated and described above in regard to a treadmill 100, other types of patient exercise machines may be used in other embodiments. That is, the loop antenna 102 may be coupled to any one of a number of different types of patient exercise machines including, but not limited to, a treadmill, a stairstepper machine, a stationary bicycle, an elliptical trainer, a rowing machine, a ski machine, or the like.

Referring now to FIG. 6, in another embodiment, the patient exercise machine 14 is illustratively embodied as a stationary bike 200. The stationary bike 200 includes a monopole antenna 202 coupled to a frame 204 of the bike 200. The monopole antenna 202 is coupled to the frame 204 in a location such that the monopole antenna 202 is in the vicinity of the orthopaedic implant 12 when the patient is operating the stationary bike 200. For example, in the illustrative embodiment of FIG. 6, the monopole antenna 202 is positioned for communication with orthopaedic implants 12 located in the lower portion of the body of the patient (e.g., a knee implant). However, in other embodiments, the monopole antenna 202 may be positioned for communication with orthopaedic implants 12 located in other portions of the patient's body. For example, in embodiments wherein the implant 12 is an orthopaedic shoulder implant, the monopole antenna 202 may be coupled to the frame 204 in a more upwardly location such as on a display panel 208 of the stationary bike 200 as indicated in FIG. 6 by monopole antenna 206. Additionally, in some embodiments, the monopole antenna 202 may be movably coupled to the frame 204 such that the location of the monopole antenna 202 relative to the patient may be altered. Additionally or alternatively, the stationary bike 200 may include multiple monopole antennas (e.g., monopole antennas 204 and 206) in some embodiments to improve the reception of the implant sensor data from the orthopaedic implant 12.

It should be appreciated that the stationary bike 200 is configured for communication with an orthopaedic implant 12 using a relatively medium data rate and carrier frequency. That is, in embodiments of the system 10 wherein the sensor 18, 66, 86 is configured to generate the implant sensor data at a data rate in the range of 100 kilobytes per second to 1,000 kilobytes per second and/or the transmitter 20, 60, 80, 414 is configured to transmit the implant sensor data using a carrier frequency in the range of 30 mega-hertz to 2,000 mega-hertz, the antenna 24 of the patient exercise machine 14 is embodied as a monopole antenna (e.g., monopole antenna 202 and/or 206). Because a relatively medium carrier frequency (e.g., in the range of 30 to 2,000 mega-hertz) is used, a larger bandwidth (relative to the embodiment illustrated and described above in regard to FIG. 5) may be used to transmit the increased amount of implant sensor data. In addition, the increased bandwidth may allow "burst" implant data signal transmission during periods when an increase in the amount of data is desired. Additionally, the monopole antenna 202 may have a decreased overall size compared to the loop antenna 102. As such, it should be appreciated that the operation of the patient exercise machine 14 by a patient may be improved by use of a monopole antenna when a relatively medium data rate (e.g., in the range of 100 kilobytes per second to 1,000 kilobytes per second) and/or a relatively medium carrier frequency (e.g., in the range of 30 to 2,000 mega-hertz) due to the decreased size of the monopole antenna.

Again, it should be appreciated that although the embodiment of FIG. 6 has been illustrated and described above in regard to a stationary bike 200, other types of patient exercise machines may be used in other embodiments. That is, the monopole antenna 202 may be coupled to any one of a number of different types of patient exercise machines including, but not limited to, a treadmill, a stairstepper machine, a stationary bicycle, an elliptical trainer, a rowing machine, a ski machine, or the like. Additionally, it should be appreciated that the monopole antenna 202 may be any type of monopole antenna 202 able to be coupled to a patient exercise machine. For example, in one particular embodiment, the monopole antenna 202 is embodied as a half-wave monopole antenna to further reduce the overall size of the antenna. In other embodiments, other types of monopole antennas, such as a quarter-wave monopole antenna, a fifth-eighths-wave monopole antenna, or the like, may be used.

Referring now to FIG. 7, in another embodiment, the patient exercise machine 14 is illustratively embodied as a stairstepper machine 300. The stairstepper machine 300 includes a patch antenna 302 coupled to a frame 304 of the stairstepper machine 300. The patch antenna 302 is coupled to or positioned in a panel 306, which is coupled to the frame 304, in a location such that the patch antenna 302 is in the vicinity of the orthopaedic implant 12 when the patient is operating the stairstepper machine 300. For example, in the illustrative embodiment of FIG. 7, the patch antenna 302 is positioned for communication with orthopaedic implants 12 located in the lower portion of the body of the patient (e.g., a knee implant). However, in other embodiments, the patch antenna 202 may be positioned for communication with orthopaedic implants 12 located in other portions of the patient's body. For example, in embodiments wherein the implant 12 is an orthopaedic shoulder implant, the patch antenna 302 may be coupled to the frame 304 in a more upwardly location such as on a display panel 308 of the stairstepper machine 300. Additionally, in some embodiments, the patch antenna 302 may be movably coupled to the frame 304 such that the location of the patch antenna 302 relative to the patient may be altered. Additionally or alternatively, the stairstepper machine 300 may include multiple patch antennas in some embodiments to improve the reception of the implant sensor data from the orthopaedic implant 12.

It should be appreciated that the stairstepper machine 300 is configured for communication with an orthopaedic implant 12 using a relatively high data rate and carrier frequency. That is, in embodiments of the system 10 wherein the sensor 18, 66, 86 is configured to generate the implant sensor data at a data rate greater than 1,000 kilobytes per second and/or the transmitter 20, 60, 80, 414 is configured to transmit the implant sensor data using a carrier frequency greater than 2 giga-hertz, the antenna 24 of the patient exercise machine 14 is embodied as a patch antenna (e.g., patch antenna 302). Because a relatively high carrier frequency (e.g., greater than 2 giga-hertz) is used, a larger bandwidth (relative to the embodiment illustrated and described above in regard to FIGS. 4 and 5) may be used to transmit the increased amount of implant sensor data. In addition, the increased bandwidth may allow and increased amount of "burst" implant data signal transmission during periods when an increase in the amount of data is desired. Additionally, the patch antenna 202 may have a decreased overall size compared to the loop antenna 102 and/or the monopole antenna 302. As such, it should be appreciated that the operation of the patient exercise machine 14 by a patient may be improved by use of a patch antenna when a relatively high data rate (e.g., greater than 1,000 kilobytes per second) and/or a relatively high carrier frequency (e.g., greater than 2 giga-hertz) due to the decreased size of the patch antenna.

Again, it should be appreciated that although the embodiment of FIG. 7 has been illustrated and described above in regard to a stairstepper machine 300, other types of patient exercise machines may be used in other embodiments. That is, the patch antenna 302 may be coupled to any one of a number of different types of patient exercise machines including, but not limited to, a treadmill, a stairstepper machine, a stationary bicycle, an elliptical trainer, a rowing machine, a ski machine, or the like.

Figure 8:
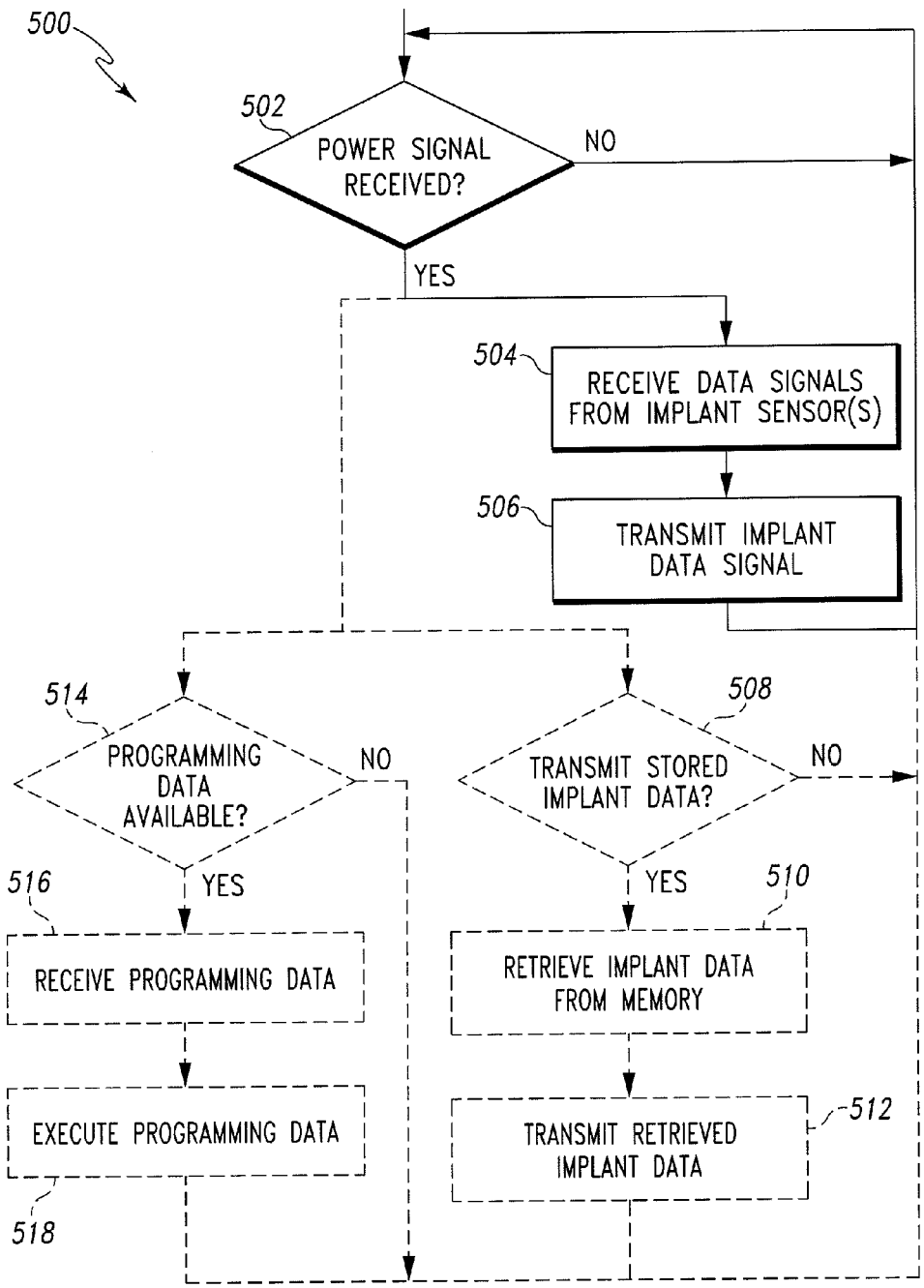
FIG. 8 is a simplified flowchart of one embodiment of an algorithm for transmitting orthopaedic implant sensor data used by an orthopaedic implant of the system of FIG. 1.

In operation, the orthopaedic implant 12 (e.g., the electronics coupled to or included in the implant 12) may be configured to execute an algorithm 500 for transmitting sensor data. As illustrated in FIG. 8, the algorithm 500 begins with a process step 502 in which the transmitter circuitry 20, 60, 80, 414 activates when a power signal has been received from the power coil 64, 84 via the communication links 70, 90. The power coil 64, 85 generates the power signal when the coil 64, 84 is inductively coupled to the primary coil 22. The algorithm 500 advances to process step 504 when a power signal has been received. In process step 504, the transmitter circuitry 20, 60, 80, 414 receives implant sensor data from the implant sensor(s) 18, 66, 86 via the communication links 72, 92. Depending on the type of the implant sensor(s) 18, 66, 86 170, the implant sensor data may be, for example, pressure data, temperature data, or the like.

Subsequently, in process step 506, the implant sensor data is transmitted by the transmitter circuitry 20, 60, 80, 414 to the antenna 24 (e.g., the loop antenna 102, the monopole antenna 202, or the patch antenna 304 depending on the particular embodiment) using the antenna 62 or the power/antenna coil 84. To do so, the transmitter circuitry 20, 60, 80, 414 may be configured to transmit the implant sensor data at a predetermined data rate or within a predetermined data rate range using a predetermined carrier frequency or range of frequencies. For example, as discussed in detail above in regard to FIG. 5, the transmitter circuitry 20, 60, 80, 414 may be configured to transmit the implant sensor data using a data rate less than 100 kilobytes per second and/or a carrier frequency less than 30,000 hertz. Alternatively, as discussed in detail above in regard to FIG. 6, the transmitter circuitry 20, 60, 80, 414 may be configured to transmit the implant sensor data using a data rate in the range of 100 kilobytes per second to 1,000 kilobytes per second and/or a carrier frequency in the range of 30 mega-hertz to 2,000 mega-hertz. Still further, as discussed in detail above in regard to FIG. 7, the transmitter circuitry 20, 60, 80, 414 may be configured to transmit the implant sensor data using a data rate greater than 1,000 kilobytes per second and/or a carrier frequency greater than 2 giga-hertz.

Once the implant sensor data from the implant sensor(s) 18, 66, 86, 402 has been transmitted, the algorithm 500 loops back to process step 502 in which the transmitter circuitry 20, 60, 80, 414 determines if another power signal has been received or is still being received from the power coil 64, 84, 410. In this way, the transmitter circuitry 20, 60, 80, 414 is configured to periodically transmit the implant sensor data while power coil 64, 84, 410 is indicatively coupled to the primary coil 22. That is, for example, while the patient is operating the patient exercise machine 14, the orthopaedic implant 12 (i.e., the transmitter circuitry 20, 60, 80, 414) will transmit implant sensor data to the antenna 24, which is received by the controller 16 via the communication links 26.

Referring back to process step 502, in some embodiments, the algorithm 500 also advances to process step 508 and 514 once a power signal has been received. In such embodiments, the process steps 504, 508, 514 may be executed in a sequential order or contemporaneously with each other once a power signal is received. In process step 508, the orthopaedic implant 12 determines if any stored implant sensor data should be transmitted to the antenna 24 (e.g., the loop antenna 102, the monopole antenna 202, the patch antenna 304 depending on the particular embodiment). To do so, the transmitter circuitry 20, 60, 80, 414 and/or processor 406, depending on the embodiment, may be programmed or otherwise configured to transmit or not transmit the stored implant sensor data. Additionally or alternatively, the transmitter circuitry 20, 60, 80, 414 and/or processor 406 may be configured to access or otherwise retrieve data from the associated memory 67, 87, 418 and determine if the stored implant sensor data should be transmitted based on such data (e.g., based on the value of the retrieved data). In this way, the orthopaedic implant 12 may be programmed to transmit stored data or not to transmit stored data depending on the particular application and/or implementation of the system 10 and/or the orthopaedic implant 12.

If the transmitter circuitry 20, 60, 80, 414 and/or processor 406 determines that any stored implant sensor data should not be transmitted in process step 508, the algorithm 500 loops back to process step 502 in which the transmitter circuitry 20, 60, 80, 414 and/or processor 406 determines if another power signal has been received or is still being received from the power coil 64, 84, 410. If, however, the transmitter circuitry 20, 60, 80, 414 and/or processor 406 determines that the implant sensor data stored in the memory device 67, 87, 418 should also be transmitted, the algorithm 500 advances to process step 510. In process step 510, the implant sensor data stored in the memory device 67, 87, 418 is retrieved. The retrieved implant sensor data is subsequently transmitted to the antenna 24 in process step 512. Once the retrieved implant sensor data has been transmitted to the antenna 24, the algorithm 500 loops back to process step 502 wherein the transmitter circuitry 20, 60, 80, 414 determines if another power signal has been received or is still being received from the power coil 64, 84, 410.

Referring back to process step 514, the orthopaedic implant 12 also determines if any programming data is available in some embodiments. In such embodiments, the transmitter circuitry 60, 80, 414 is embodied as or otherwise includes a transceiver configured to transmit and receive data from the antenna 24. If the transmitter circuitry 20, 60, 80, 414 and/or processor 406 determines that programming data is not available in process step 514, the algorithm 500 loops back to process step 502 in which the transmitter circuitry 20, 60, 80, 414 determines if another power signal has been received or is still being received from the power coil 64, 84, 410. If, however, the transmitter circuitry 20, 60, 80, 414 and/or processor 406 determines that the programming data is available, the algorithm 500 advances to process step 516. In process step 516, the orthopaedic implant 12 receives programming data from the controller 16 via the antenna 24. Subsequently, in process step 518, the transmitter circuitry 20, 60, 80, 414 and/or processor 406 is configured to update one or more programs or programming data used by the electronic circuitry of the orthopaedic implant 12. For example, in embodiments wherein the orthopaedic implant 12 is embodied as the implant 12 illustrated in and described above in regard to FIG. 4, the programming data may be used by the processor 406 to control the switching circuit 400 such that the implant sensor data from any one or more implant sensors 402 may be monitored.

Figure 9:
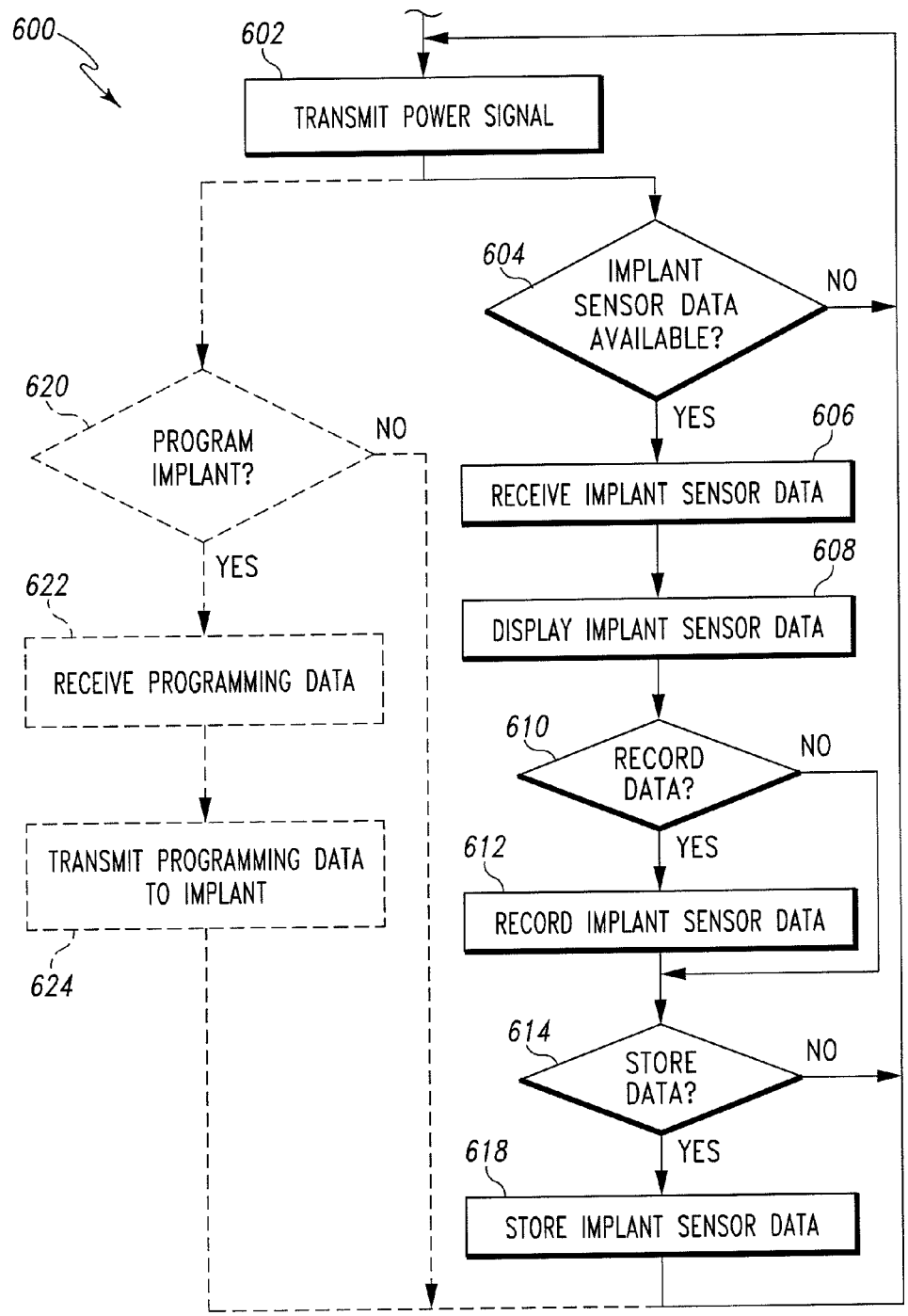
FIG. 9 is a simplified flowchart of one embodiment of an algorithm for monitoring orthopaedic implant sensor data used by the system of FIG. 1.

Referring now to FIG. 9, in use, the controller 16 of the system 10 may execute an algorithm 600 for monitoring orthopaedic implant data. 10. The algorithm 600 begins with a process step 602 in which the primary coil 22 of the patient exercise machine 14 is inductively coupled with the secondary coil (e.g., the power coil 64 or the power/antenna coil 84) of the orthopaedic implant 12. To do so, the controller 16 is configured to transmit a power signal to the primary coil 22 via the communication link 28 to thereby energize the coil 22. In response, the primary coil 22 generates the electromagnetic field 48, which is received by the secondary coil (e.g., the power coil 64 or the power/antenna coil 84) of the orthopaedic implant 12. It should be appreciated that the controller 16 may be configured to continuously energize the primary coil 22, periodically energize the primary coil 22, or selectively energize the primary coil 22. For example, in some embodiments, the patient exercise machine 14 may include a pressure or motion sensor configured to determine the presence of the patient. In such embodiments, the pressure, motion, or other sensor output is transmitted to the controller 16 and, in response, the controller 16 transmits the power signal to the primary coil 22. In this way, the primary coil 22 is only energized when a patient is operating or in the vicinity of the patient exercise machine 14.

Once the power signal has been transmitted to the power coil 22, the controller 16 determines if any implant sensor data is available (i.e., if any implant sensor data is being transmitted) in process step 604. If not, the algorithm 600 loops back to the process step 602 wherein the controller 16 continuously, periodically, or selectively transmits the power signal to the primary coil 22. However, if implant sensor data is being transmitted by the orthopaedic implant 12, the algorithm 600 advances to process step 606. In process step 606, the implant sensor data is received from the orthopaedic implant 12. That is, the implant sensor data is received by the antenna 24 (e.g., the loop antenna 102, the monopole antenna 202, or the patch antenna 302) of the patient exercise machine 14 and transmitted to the controller 16 via the communication links 26.

Once the implant sensor data has been received in process step 606, the implant sensor data is displayed to the healthcare provider on the display device 34. To do so, the controller 16 is configured to transmit the implant sensor data to the display device 34 via the communication links 36. Additionally or alternatively, the controller 16 may be configured to calculate or determine other data based on the implant sensor data. For example, in some embodiments, the controller 16 may be configured to determine a graph or chart based on the implant sensor data received from the orthopaedic implant sensor 12 and display the graph or chart to the healthcare provider on the display device 34.

Once the implant sensor has been displayed to the healthcare provider in process step 608, the controller 16 determines if the healthcare provider desires to record the implant sensor data in process step 610. The healthcare provider may require that the implant sensor data be recorded by supplying the appropriate commands to the controller 16 via, for example, a keyboard, mouse, or other input device. Alternatively, the controller 16 may be configured to always record the implant sensor data. Regardless, if the controller 16 has determined that the implant sensor data is to be recorded, the algorithm 600 advances to process step 612. In process step 612, the implant sensor data received from the orthopaedic implant sensor 12 is temporarily stored in the memory device 32 or other storage location (e.g., hard drive, floppy disk, portable memory device, etc.) of the controller 16. The implant sensor data may be recorded for use in many different applications such as, for example, for calculating or determining other data such as a graph or chart of implant data received over a predetermined period of time or as temporary storage.

Once the implant sensor data has been recorded in process step 612 or if the controller 16 determined that the implant sensor data should not be recorded in process step 610, the algorithm 600 advances to process step 614. In process step 614, the controller 16 determines if the healthcare provider desires to store the implant sensor data. As described above, the healthcare provider may require that the implant sensor data be stored by supplying the appropriate commands to the controller 16 via, for example, a keyboard, mouse, or other input device. Alternatively, the controller 16 may be configured to always store the implant sensor data. Regardless, if the controller 16 has determined that the implant sensor data is to be stored, the algorithm 600 advances to process step 618. In process step 618, the controller 16 transmits the implant sensor data received from the orthopaedic implant sensor 12 to the patient database 40 via the communication links 44, the network 42, and the communication links 46. The implant sensor data may be stored in the patient database 40 for later use such as for examination by an orthopaedic surgeon or other healthcare provider. In addition, because the patient database 40 forms a portion of a hospital network in some embodiments, the implant sensor data may be accessible from other locations (e.g., an orthopaedic surgery room) in the hospital once stored in the database 40. Once the implant sensor data has been stored in process step 618 or if the controller 16 has determined that the implant sensor data should not be stored in process step 614, the algorithm 600 loops back to process step 602 in which the controller 16 is configured to transmit the power signal to the primary coil 22.

Referring back to process step 602, the controller 16 is also configured to determine if the orthopaedic healthcare provider desires to program the orthopaedic implant in a process step 620 in some embodiments. If not, the algorithm 600 loops back to the process step 602 wherein the controller 16 continuously, periodically, or selectively transmits the power signal to the primary coil 22. However, if controller 16 determines that the orthopaedic healthcare provider desires to program the orthopaedic implant 12 in process step 620, the algorithm 600 proceeds to process step 622. In process step 622, the orthopaedic healthcare provider supplies the programming data to the controller 16. The orthopaedic healthcare provider may supply the programming data via manually typing in the data or otherwise operating the controller 16 such that the programming data is transmitted to the orthopaedic implant 12 via the antenna 24. Once the orthopaedic healthcare provider has entered or otherwise supplied the programming data via the controller 16, the programming data is transmitted to the orthopaedic implant 12 via the antenna 24 in process step 624. As discussed above, the programming data may cause the orthopaedic implant 12 to transmit implant sensor data generated by one or more implant sensors 402 selected by the orthopaedic healthcare provider. In this way, the orthopaedic healthcare provider may individually monitor each of the orthopaedic implant sensors 402 while the patient is exercising on the patient excise machine 14.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, although specific data rate values and ranges and specific frequency values and ranges have been disclosed in various embodiments, it should be appreciated that data rates and/or frequencies near such values may be in used in other embodiments.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A system for monitoring implant sensor data, the system comprising:
   an orthopaedic implant;
   a secondary coil coupled to the orthopaedic implant;
   a sensor secured to the orthopaedic implant and configured to generate implant sensor data;
   a transmitter coupled to the orthopaedic implant and electrically coupled to the secondary coil and to the sensor, the transmitter being configured to wirelessly transmit the implant sensor data at a data rate of less than 100 kilobytes per second;
   a patient exercise machine;
   a loop antenna secured to the patient exercise machine and configured to receive the implant sensor data;
   a controller electrically coupled to the loop antenna and configured to (i) receive the implant sensor data from the loop antenna and (ii) display indicia of the implant sensor data on a display device; and
   a primary coil electrically coupled to the controller,
   wherein the transmitter wirelessly transmits the implant sensor data and the controller receives the implant sensor data from the loop antenna and displays indicia of the implant sensor data on the display device in response to a power signal received from the secondary coil when the secondary coil is inductively coupled with the primary coil.

2. The system of claim 1, wherein the sensor is a sensor selected from the group consisting of: a pressure sensor, a load sensor, a temperature sensor, and a hall-effect sensor.

3. The system of claim 1, wherein the transmitter is configured to transmit the implant sensor data using a predetermined carrier frequency of lower than 30,000 hertz.

4. The system of claim 1, wherein the patient exercise machine is an exercise machine selected from the group consisting of: a treadmill, a stairstepper machine, a stationary bicycle, an elliptical trainer, a rowing machine, and a ski machine.

5. The system of claim 1, the controller is configured to record the implant sensor data.

6. The system of claim 1, wherein the controller is configured to transmit the implant sensor data to a database over a network and store the implant sensor data in the database.

7. The system of claim 1, wherein:
   (i) the transmitter forms a portion of a transceiver;
   (ii) the controller is configured to transmit programming data to the transceiver; and
   (iii) the transceiver is configured to transmit implant sensor data from one of a number of implant sensors selected based on the programming data.

8. A system for monitoring implant sensor data, the system comprising:
- an orthopaedic implant;
- a secondary coil coupled to the orthopaedic implant;
- a sensor secured to the orthopaedic implant and configured to generate implant sensor data;
- a transmitter coupled to the orthopaedic implant and electrically coupled to the secondary coil and to the sensor, the transmitter being configured to wirelessly transmit the implant sensor data at a data rate in the range of 100 kilobytes per second to 1,000 kilobytes per second;
- a patient exercise machine;
- a monopole antenna secured to the patient exercise machine and configured to receive the implant sensor data;
- a controller electrically coupled to the monopole antenna and configured to receive the implant sensor data from the monopole antenna and (ii) display indicia of the implant sensor data on a display device; and
- a primary coil electrically coupled to the controller,
- wherein the transmitter wirelessly transmits the implant sensor data and the controller receives the implant sensor data from the monopole antenna and displays indicia of the implant sensor data on the display device in response to a power signal received from the secondary coil when the secondary coil is inductively coupled with the primary coil.

9. The system of claim 8, wherein the sensor is a sensor selected from the group consisting of: a pressure sensor, a load sensor, a temperature sensor, and a hall-effect sensor.

10. The system of claim 8, wherein the transmitter is configured to transmit the implant sensor data using a predetermined carrier frequency in the range of 30 mega-hertz to 2,000 mega-hertz.

11. The system of claim 8, wherein the patient exercise machine is an exercise machine selected from the group consisting of: a treadmill, a stairstepper machine, a stationary bicycle, an elliptical trainer, a rowing machine, and a ski machine.

12. The system of claim 8, wherein the monopole antenna is an antenna selected from the group consisting of: a quarter-wave monopole antenna, a half-wave monopole antenna, and a five-eighths-wave monopole antenna.

13. The system of claim 8, wherein the controller is configured to transmit the implant sensor data to a database over a network and store the implant sensor data in the database.

14. The system of claim 8, wherein:
(i) the transmitter forms a portion of a transceiver;
(ii) the controller is configured to transmit programming data to the transceiver; and
(iii) the transceiver is configured to transmit implant sensor data from one of a number of implant sensors selected based on the programming data.

15. A system for monitoring implant sensor data, the system comprising:
- an orthopaedic implant;
- a secondary coil coupled to the orthopaedic implant;
- a sensor secured to the orthopaedic implant and configured to generate implant sensor data;
- a transmitter coupled to the orthopaedic implant and electrically coupled to the secondary coil and to the sensor, the transmitter being configured to wirelessly transmit the implant sensor data at a data rate greater than 1,000 kilobytes per second;
- a patient exercise machine;
- a patch antenna secured to the patient exercise machine and configured to receive the implant sensor data;
- a controller electrically coupled to the patch antenna and configured to (i) receive the implant sensor data from the patch antenna and (ii) display indicia of the implant sensor data on a display device; and
- a primary coil electrically coupled to the controller,
- wherein the transmitter wirelessly transmits the implant sensor data and the controller receives the implant sensor data from the patch antenna and displays indicia of the implant sensor data on the display device in response to a power signal received from the secondary coil when the secondary coil is inductively coupled with the primary coil.

16. The system of claim 15, wherein the transmitter is configured to transmit the implant sensor data using a predetermined carrier frequency greater than 2 giga-hertz.

17. The system of claim 15, wherein:
(i) the transmitter forms a portion of a transceiver;
(ii) the controller is configured to transmit programming data to the transceiver; and
(iii) the transceiver is configured to transmit implant sensor data from one of a number of implant sensors selected based on the programming data.

* * * * *